United States Patent
Ryu et al.

(10) Patent No.: US 9,399,212 B2
(45) Date of Patent: Jul. 26, 2016

(54) METHOD FOR PRODUCING ANHYDROSUGAR ALCOHOL THROUGH CONTINUOUS DEHYDRATION REACTION OF HYDROGENATED SUGAR

(71) Applicant: SAMYANG CORPORATION, Seoul (KR)

(72) Inventors: Hoon Ryu, Daejeon (KR); Young Jae Jung, Daejeon (KR); Jin Kyung Kim, Daejeon (KR); Do Hyun Kyung, Daejeon (KR); Hyuk Min Park, Incheon (KR); Seong Ho Cho, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 14/763,114

(22) PCT Filed: Feb. 21, 2014

(86) PCT No.: PCT/KR2014/001402
§ 371 (c)(1),
(2) Date: Jul. 23, 2015

(87) PCT Pub. No.: WO2014/129833
PCT Pub. Date: Aug. 28, 2014

(65) Prior Publication Data
US 2015/0353574 A1    Dec. 10, 2015

(30) Foreign Application Priority Data

Feb. 22, 2013  (KR) .................... 10-2013-0019105

(51) Int. Cl.
*B01J 31/10*    (2006.01)
*C07D 493/04*    (2006.01)

(52) U.S. Cl.
CPC .............. *B01J 31/10* (2013.01); *C07D 493/04* (2013.01)

(58) Field of Classification Search
CPC ........................................................ B01J 31/10
USPC ............................................................. 549/464
See application file for complete search history.

(56) References Cited

U.S. PATENT DOCUMENTS 6,639,067 B1  10/2003  Brinegar et al.
7,439,352 B2  10/2008  Moore et al.

FOREIGN PATENT DOCUMENTS

| KR | 2001-0079763 A | 8/2001 |
| KR | 10-2011-0076268 A | 7/2011 |
| KR | 10-1079518 B1 | 11/2011 |
| KR | 10-2012-0066904 A | 6/2012 |
| WO | WO 2012/081785 A1 | 6/2012 |

OTHER PUBLICATIONS

International Search Report issued in PCT/KR2014/001402, mailed on Jun. 23, 2014.

*Primary Examiner* — Taofiq A Solola
(74) *Attorney, Agent, or Firm* — Birch, Stewart, Kolasch & Birch, LLP

(57) ABSTRACT

The present invention relates to a method for producing an anhydrosugar alcohol and, more specifically, to a method for producing an anhydrosugar alcohol which, when the step of subjecting a hydrogenated sugar to a dehydration reaction in a reactor so as to convert same to an anhydrosugar alcohol is performed, allows the hydrogenated sugar to be continuously introduced into the reactor and the produced anhydrosugar alcohol to be continuously discharged out of the reactor while the dehydration reaction is carried out, also prevents a reaction mixture from circulating inside and outside the reactor while the dehydration reaction is carried out, and thereby can significantly improve production efficiency compared with a conventional process adopting a batch or semi-batch-type dehydration reaction and thus can be appropriately applied particularly to a large-scale anhydrosugar alcohol production process.

12 Claims, No Drawings

METHOD FOR PRODUCING ANHYDROSUGAR ALCOHOL THROUGH CONTINUOUS DEHYDRATION REACTION OF HYDROGENATED SUGAR

TECHNICAL FIELD

The present invention relates to a method for producing anhydrosugar alcohol, and more specifically a method for producing anhydrosugar alcohol comprising the step of converting hydrogenated sugar to anhydrosugar alcohol by dehydration reaction in a reactor, wherein while the dehydration reaction is conducted, the hydrogenated sugar is continuously fed into the reactor and the produced anhydrosugar alcohol is continuously discharged out of the reactor, and the reaction mixture is not circulated in and out of the reactor during the conduction of the dehydration reaction. As compared with conventional processes employing a batch-type or semi-hatch-type dehydration reaction, the present method can remarkably improve the production efficiency and, in particular, it can be suitably applied in a large-scale process for producing anhydrosugar alcohol.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the carbon number, hydrogenated sugar is classified into tetritol, pentitol, hexitol and heptitol (4, 5, 6 and carbons, respectively). Among them, hexitol having 6 carbons includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, medicaments such as patch adhesive, mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

As such, anhydrosugar alcohol is receiving much interest because of its wide applicability, and the level of practical industrial application thereof is increasing. However, the conventional methods of producing anhydrosugar alcohol have limitations of high cost for the catalyst used in the dehydration reaction, low conversion rate, and low yields of distillation and purification, etc.

In particular, conventional processes have mainly used a method for converting hydrogenated sugar to anhydrosugar alcohol through batch-type reaction. However, such a method has the problems of difficulty in working, increase of working time, and excessive enlargement of reactor size for production with industrial capacity. As an alternative, there is a semi-batch-type method wherein plural batch-type reactors are connected and operated in a continuous manner. However, this method also has the problems of difficulty in working, increase of working time, difficulty in temperature setting for each step, and more complicated facilities.

Therefore, there is a need to develop a method for producing anhydrosugar alcohol which can improve the production efficiency through a new manner of operation and can be utilized suitably in a large-scale, commercial production process.

CONTENTS OF THE INVENTION

Problems to be Solved

To resolve the problems of the prior arts as explained above, the present invention has an object of providing a method for producing anhydrosugar alcohol, employing a new manner of operation different from conventional batch-type or semi-batch-type dehydration reaction when conducting the step of converting hydrogenated sugar to anhydrosugar alcohol by dehydration reaction, which can remarkably improve the production efficiency and provide a reaction product having a quality that is the same as or better than those of conventional processes, and thus in particular, can be suitably applied in a large-scale process for producing anhydrosugar alcohol.

Technical Means

To achieve the above-stated object, the present invention provides a method for producing anhydrosugar alcohol comprising the step of converting hydrogenated sugar to anhydrosugar alcohol by dehydration reaction in a reactor, wherein while the dehydration reaction is conducted, the hydrogenated sugar is continuously fed into the reactor and the produced anhydrosugar alcohol is continuously discharged out of the reactor, and the reaction mixture is not circulated in and out of the reactor during the conduction of the dehydration reaction.

Effect of the Invention

If hydrogenated sugar is converted to anhydrosugar alcohol through the continuous dehydration reaction according to the present invention, it is possible to improve the production efficiency remarkably as compared with conventional batch-type or semi-batch-type processes, provide a reaction product having a quality that is the same as or better than those of conventional processes, and decrease the time required for connecting to the subsequent procedures. Therefore, in particular, the method for producing anhydrosugar alcohol of the present invention can be suitably applied in a large-scale process for producing anhydrosugar alcohol.

CONCRETE EXPLANATION TO CARRY OUT THE INVENTION

The present invention is explained in more detail below.

In the method for producing anhydrosugar alcohol of the present invention, while the dehydration reaction is conducted, the hydrogenated sugar is continuously fed into the reactor and the produced anhydrosugar alcohol is continuously discharged out of the reactor. That is, while the dehydration reaction in the present invention is conducted, a continuous flow by the reaction mixture is formed within the reactor.

The flow rate of the reaction mixture forming a continuous flow within the reactor during the dehydration reaction can be selected properly according to the concrete specifications of the reactor and other conditions for operation. Therefore, although a flow rate of 2 to 4 mL/minute was applied when using a reactor of 1 L size in the present working examples, it is not limited thereto, and a skilled artisan could easily select a suitable flow rate according to an enlargement of facilities and/or a change in other conditions for operation.

The continuous flow formed within the reactor during the dehydration reaction, may preferably be steady state flow. As used herein, "steady state flow" corresponds to a state in which no substantial change in the reaction system is observed by an outside observer—i.e., a state in which the feeding rate of material into the reactor and discharge rate of material out of the reactor are substantially the same. As used herein, "substantially the same" means that the feeding rate of material into the reactor is, for example, 0.95 to 1.05 times, more preferably 0.99 to 1.01 times the discharge rate of material out of the reactor, and most preferably they are the same.

In the present invention, the reaction mixture is not circulated in and out of the reactor while the dehydration reaction is conducted. Some conventional prior arts employ a process wherein a dehydration reactor is line-connected with a separate outer device(s) (e.g., heat exchanger, etc.) and while the dehydration reaction is conducted, a part of the material in the reactor is discharged out of the reactor, passed through the outer device and reintroduced into the reactor. Such a circulation process of the reaction mixture has advantages of supplying additional heat source into the reactor and conducting the additional function of agitation, etc. However, it has disadvantages of difficulty in overall control of the flow amount of material which is continuously fed into the reactor, and disturbance of formation of uniform continuous flow within the reactor due to the irregularity generated by the circulation of liquid. Accordingly, the present invention does not circulate the reaction mixture in and out of the reactor while the dehydration reaction is conducted, thereby the continuous feeding of material into the reactor can be easily controlled and the uniform continuous flow can be formed within the reactor.

The continuous dehydration reaction of the present invention can be conducted in a single reactor, or by using a facility wherein two or more reactors are serially connected, if necessary. In the case of using two or more serially connected reactors, they are recognized as one reactor as a whole, and the continuous flow formed during the dehydration reaction is maintained throughout the whole reactors.

The inside of the reactor where the continuous dehydration reaction of the present invention is conducted may be divided into two or more sections, if necessary, and the operation conditions such as temperature, pressure, etc. for each section may be controlled independently. In the case of operation with two or more serially connected reactors, each reactor may correspond to each of the above-mentioned sections. In this case, the feeding/discharge rates of material for each section (or each reactor) may be set differently according to necessity, but the overall continuous flow is maintained.

In the present invention, the continuous dehydration reaction of hydrogenated sugar can be conducted, for example, under a temperature condition of from 105 to 200° C. (more preferably, 110 to 150° C.) and a pressure condition of from 1 to 100 mmHg (more preferably, 1 to 50 mmHg) for 1 to 10 hours (more preferably, 2 to 5 hours), but it is not limited thereto. As stated earlier, in the case of dividing the inside of the reactor—where the continuous dehydration reaction is conducted—into two or more sections, the operation conditions such as temperature, pressure, etc. for each section may be controlled independently within the above ranges. According to an embodiment of the present invention, in the case of dividing the inside of the reactor into two or more sections, based on the reaction mixture flow, it is preferable to set the reaction temperature of the latter section lower than that of the former section since it is possible thereby to reduce byproducts which may be generated drastically due to overheating in the latter part of the reaction.

Hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol, having 6 carbons, includes sorbitol, mannitol, iditol, galactitol, etc.—in particular, sorbitol and mannitol are very useful materials.

As used herein, the expression "anhydrosugar alcohol" means any material that is obtained by removing one or more water molecules from the original inner structure of said hydrogenated sugar (or sugar alcohol) in one or more steps by any method.

In the present invention, hexitol is preferably used as the hydrogenated sugar, and more preferably, the hydrogenated sugar for use is selected from sorbitol, mannitol, iditol and mixtures thereof.

Accordingly, in the present invention, dianhydrohexitol—which is the dehydrated product of hexitol—is preferably obtained as the anhydrosugar alcohol, and more preferably, the obtained anhydrosugar alcohol is selected from isosorbide (1,4-3,6-dianhydrosorbitol), isomannide (1,4-3,6-dianhydromannitol), isoidide (1,4-3,6-dianhydroiditol) and mixtures thereof. Among them, isosorbide is particularly useful for industrial and medicinal application.

It is preferable to use an acid catalyst in dehydrating hydrogenated sugar to convert it to anhydrosugar alcohol.

According to an embodiment of the present invention, as for the acid catalyst a single acid catalyst such as sulfuric acid, nitric acid, hydrochloric acid, p-toluenesulfonic acid, phosphoric acid, etc. can be used, and more preferably, sulfuric acid can be used.

According to the other embodiment of the present invention, as for the acid catalyst an acid mixture of a first acid and a second acid can be used, and more preferably, sulfuric acid can be used as the first acid, and one or more sulfur-containing acid materials selected from the group consisting of p-toluenesulfonic acid, methanesulfonic acid, ethanesulfonic acid, benzenesulfonic acid, naphthalenesulfonic acid and aluminum sulfate can be used as the second acid.

The acid catalyst is preferably used in an amount of from 0.5 to 10 parts by weight per 100 parts by weight of the hydrogenated sugar (e.g., hexitol). If the amount of acid catalyst is much less than the above range, the conversion time to anhydrosugar alcohol may become excessively long. On the other hand, if the amount of acid catalyst is much greater than the above range, sugar polymer may be increasingly generated and the conversion rate may be lowered.

In the case of using an acid catalyst during the dehydration reaction of hydrogenated sugar, it is preferable to neutralize the reaction product liquid. The neutralization may be conducted after the dehydration reaction by cooling the reaction product liquid (e.g., to 100° C. or lower) and adding thereto conventional alkali such as sodium hydroxide. The neutralized reaction product liquid preferably has a pH of 6 to 8.

The neutralized reaction product liquid as obtained above can go through distillation after being pre-treated, if necessary, and subsequent purification procedure to produce an anhydrosugar alcohol product with high purity.

The purpose of the pre-treatment is to remove moisture and a low-boiling-point substance(s) remaining in the resulting liquid of the converting step before being fed to the subsequent distilling step, and may be conducted conventionally at a temperature of from 90° C. to 110° C. under a pressure of 10 mmHg to 100 mmHg for 1 hour or longer (e.g., 1 to 4 hours), but it is not limited thereto. The pre-treatment procedure for removing moisture, etc. from the resulting liquid of the converting step may be conducted by using a degasser or flash box, or by a method of removing water by vacuum in the storage tank, but it is not limited thereto.

There is no special limitation in the distillation of the resulting liquid of the converting step, and any conventionally known method and device in this field may be utilized as it is or with proper modification. For example, a general condenser-type evaporator or column distillator may be used, or a thin-film evaporator may be utilized for the distillation.

The subsequent purification procedure for the resulting liquid of distillation may be one or more selected from crystallization, decolorization and treatment with ion exchange resin, but it is not limited thereto. There is no special limitation in the order thereof. For these subsequent purification procedures, with no special limitation, any conventionally known method and device in this field for the corresponding treatment procedure may be utilized as it is or with proper modification.

According to an embodiment of the present invention, the distillation may be conducted with using a thin-film evaporator, and the crystallization may be conducted by a crystallization method using a solvent (e.g., acetone solvent) or by a melt crystallization method using no solvent. The decolorization may be conducted with using active carbon, and the treatment with ion exchange resin may be conducted with using strong cationic ion exchange resin, strong anionic ion exchange resin, or all of them in this order.

The present invention is explained in more detail through the following Examples and Comparative Example. However, the Examples are intended to facilitate understanding of the present invention only, and the scope of the present invention is not limited thereby.

EXAMPLES

Example 1

The reaction facility for conducting the continuous dehydration reaction was constituted as follows. First, two reactors of 1 L size equipped with an agitation rod, a condenser and a thermometer (for measuring the inner temperature) were prepared, the upper parts of each condenser were connected with a depressurizing device, and the two reactors were connected with each other by using heat-resistant silicone tube and adaptor. Next, one of the two reactors (Reactor 1) was connected with a vessel containing a liquid mixture of melted sorbitol liquid maintained at 120° C. and catalyst (vessel for feeding raw material) by using heat-resistant silicone tube and adaptor, and the other reactor (Reactor 2) was connected with a vessel for collecting reaction liquid—to which a flask for receiving distillate and a condenser were connected—by using heat-resistant silicone tube and adaptor. Each silicone tube between the reactors and vessels passed through a peristaltic pump to allow the reaction mixture to be transferred continuously.

The continuous dehydration reaction was conducted as follows. First, in order to realize the continuous flow state of the reaction mixture, each of Reactors 1 and 2 was filled with 300 mL of a reaction liquid containing 71.2% of isosorbide, the temperature of Reactor 1 was set to 150° C. and the temperature of Reactor 2 was maintained at 140° C. or lower, and the pump was operated without depressurization to fill the reaction liquid in all connection tubes. Next, the pump was operated under reduced pressure condition to start transfer of the melted liquid mixture of sorbitol and catalyst (sulfuric acid and methanesulfonic acid) from the vessel for feeding raw material to Reactor 1 at a constant rate. While the reaction was conducted, both the rate of feeding the raw material mixture liquid into Reactor 1 and the rate of discharging the reaction product out of Reactor 2 were maintained at 3 mL per minute. The retention time of the reaction mixture liquid in reactor (=volume of the reaction liquid mixture/flow rate) was 200 minutes in total. The target content of isosorbide was set to 71%.

Samples were taken from the vessel for collecting reaction liquid at a constant time interval and analyzed by a gas chromatography method to obtain isosorbide contents in the reaction mixture liquid over time. The results are shown in Table 1.

TABLE 1

| Time (hr) | 0.0 | 1.0 | 2.0 | 3.0 | 4.0 | 4.8 |
|---|---|---|---|---|---|---|
| Isosorbide content (%) | 71.2 | 71.4 | 70.8 | 71.2 | 70.9 | 71.3 |

As can be seen from the above Table 1, during the conduction of continuous dehydration reaction targeting the isosorbide content to 71%, the actual isosorbide content was maintained stably within the range of from 70.8 to 71.4%.

Example 2

The continuous dehydration reaction was conducted by using the same facility as that of Example 1, other than the fact that the volume of the reaction liquid (isosorbide content: 71.2%) in Reactor 1 was 500 mL, the volume of the reaction liquid in Reactor 2 was 200 mL, the rate of feeding the raw material mixture liquid into Reactor 1 was 4 mL per minute, and the rate of discharging the reaction product out of Reactor 2 was 2 mL per minute. The retention time was 225 minutes in total (125 minutes in Reactor 1 and 100 minutes in Reactor 2). The target content of isosorbide was set to 71%.

Samples were taken from the vessel for collecting reaction liquid at a constant time interval and analyzed by a gas chromatography method to obtain isosorbide contents in the reaction mixture liquid over time. The results are shown in Table 2.

TABLE 2

| Time (hr) | 0.0 | 1.3 | 2.2 | 3.0 | 3.8 |
|---|---|---|---|---|---|
| Isosorbide content (%) | 71.2 | 70.6 | 71.0 | 70.8 | 70.5 |

As can be seen from the above Table 2, during the conduction of continuous dehydration reaction targeting the isosorbide content to 71%, the actual isosorbide content was maintained stably within the range of from 70.5 to 71.2%.

Example 3

The continuous dehydration reaction was conducted by using the same facility as that of Example 1, other than the fact that the volume of the reaction liquid (isosorbide content: 71.2%) in Reactor 1 was 200 mL, the volume of the reaction liquid in Reactor 2 was 200 mL, and both the rate of feeding the raw material mixture liquid into Reactor 1 and the rate of discharging the reaction product out of Reactor 2 were 2 mL per minute. The retention time was 200 minutes in total. The target content of isosorbide was set to 71%.

Samples were taken from the vessel for collecting reaction liquid at a constant time interval and analyzed by a gas chromatography method to obtain isosorbide contents in the reaction mixture liquid over time. The results are shown in Table 3.

TABLE 3

| Time (hr) | 0.0 | 1.1 | 2.3 | 3.2 | 4.2 | 4.8 |
|---|---|---|---|---|---|---|
| Isosorbide content (%) | 71.2 | 70.8 | 70.9 | 72.0 | 71.3 | 71.0 |

As can be seen from the above Table 3, during the conduction of continuous dehydration reaction targeting the isosorbide content to 71%, the actual isosorbide content was maintained stably within the range of from 70.8 to 72.0%.

Example 4

The continuous dehydration reaction was conducted by using the same facility as that of Example 1, other than the fact that the volume of the reaction liquid (isosorbide content: 71.2%) in Reactor 1 was 370 mL and the volume of the reaction liquid in Reactor 2 was 370 mL. Both the rate of feeding the raw material mixture liquid into Reactor 1 and the rate of discharging the reaction product out of Reactor 2 were 3 mL per minute. The retention time was 250 minutes in total. The target content of isosorbide was set to 71%.

Samples were taken from the vessel for collecting reaction liquid at a constant time interval and analyzed by a gas chromatography method to obtain isosorbide contents in the reaction mixture liquid over time. The results are shown in Table 4.

TABLE 4

| Time (hr) | 0.0 | 0.8 | 1.8 | 2.5 | 3.3 | 4.0 |
|---|---|---|---|---|---|---|
| Isosorbide content (%) | 71.2 | 70.7 | 71.3 | 70.6 | 70.7 | 70.9 |

As can be seen from the above Table 4, during the conduction of continuous dehydration reaction targeting the isosorbide content to 71%, the actual isosorbide content was maintained stably within the range of from 70.6 to 71.3%.

Comparative Example 1

800 g of sorbitol powder was fed into a 4-necked glass reactor, and an agitator, a condenser, a flask for receiving distillate and a thermometer were connected thereto. The sorbitol was melted by heating. To the melted liquid at 110° C., 8 g of sulfuric acid and 3.4 g of methanesulfonic acid were added, and the dehydration reaction was conducted under a reduced pressure condition of 35 mmHg or less while heating to maintain the inner temperature at 130 to 135° C. for about 3 hours. After the dehydration reaction was completed, a sample was taken and analyzed by a gas chromatography method. The isosorbide content in the resulting liquid of reaction was 71.0%.

As can be seen from the above Examples, in the case of producing anhydrosugar alcohol by the continuous dehydration reaction according to the present invention, the isosorbide content in the reaction mixture liquid could be maintained very stably at the target level during the conduction of the continuous process. Therefore, it was confirmed that according to the present invention, a reaction product having a quality that is the same as or better than those of conventional processes can be provided while remarkably improving the production efficiency as compared with conventional batch-type or semi-batch-type processes.

The invention claimed is:

1. A method for producing anhydrosugar alcohol comprising the step of converting hydrogenated sugar to anhydrosugar alcohol by dehydration reaction in a reactor, wherein while the dehydration reaction is conducted, the hydrogenated sugar is continuously fed into the reactor and the produced anhydrosugar alcohol is continuously discharged out of the reactor, and the reaction mixture is not circulated in and out of the reactor during the conduction of the dehydration reaction.

2. The method for producing anhydrosugar alcohol according to claim 1, wherein while the dehydration reaction of the hydrogenated sugar is conducted, a continuous flow by the reaction mixture is formed within the reactor.

3. The method for producing anhydrosugar alcohol according to claim 2, wherein the continuous flow is steady state flow.

4. The method for producing anhydrosugar alcohol according to claim 1, wherein the feeding rate of the hydrogenated sugar into the reactor is 0.95 to 1.05 times the discharge rate of the anhydrosugar alcohol out of the reactor.

5. The method for producing anhydrosugar alcohol according to claim 1, wherein the dehydration reaction of the hydrogenated sugar is conducted in a single reactor, or by using a facility wherein two or more reactors are serially connected.

6. The method for producing anhydrosugar alcohol according to claim 5, wherein the dehydration reaction of the hydrogenated sugar is conducted by using a facility wherein two or more reactors are serially connected, and during the dehydration reaction, a continuous flow by the reaction mixture is formed and maintained throughout the whole reactors.

7. The method for producing anhydrosugar alcohol according to claim 1, wherein an acid catalyst is used in the step of converting hydrogenated sugar to anhydrosugar alcohol by dehydration reaction.

8. The method for producing anhydrosugar alcohol according to claim 7, wherein the acid catalyst is a single acid catalyst selected from sulfuric acid, nitric acid, hydrochloric acid, p-toluenesulfonic acid and phosphoric acid; or the acid catalyst is an acid mixture of a first acid and a second acid wherein the first acid is sulfuric acid and the second acid is one or more sulfur-containing acid materials selected from the group consisting of p-toluenesulfonic acid, methanesulfonic acid, ethanesulfonic acid, benzenesulfonic acid, naphthalenesulfonic acid and aluminum sulfate.

9. The method for producing anhydrosugar alcohol according to claim 1, further comprising neutralization of the resulting liquid of the dehydration reaction of hydrogenated sugar.

10. The method for producing anhydrosugar alcohol according to claim 9, further comprising distillation of the neutralized resulting liquid of the dehydration reaction of hydrogenated sugar after removal of moisture therefrom.

11. The method for producing anhydrosugar alcohol according to claim 10, wherein the distillation is conducted by using a thin-film evaporator.

12. The method for producing anhydrosugar alcohol according to claim 10, further comprising purification of the resulting liquid of distillation by one or more procedures selected from crystallization, decolorization and treatment with ion exchange resin.

* * * * *